(12) United States Patent
Melsheimer et al.

(10) Patent No.: US 11,744,985 B2
(45) Date of Patent: *Sep. 5, 2023

(54) STEERABLE CATHETER SYSTEM WITH HUB

(71) Applicant: Cook Medical Technologies LLC, Bloomington, IN (US)

(72) Inventors: Jeffry Scott Melsheimer, Springville, IN (US); Patrick James Zito, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 362 days.

This patent is subject to a terminal disclaimer.

(21) Appl. No.: 17/089,232

(22) Filed: Nov. 4, 2020

(65) Prior Publication Data

US 2021/0046282 A1 Feb. 18, 2021

Related U.S. Application Data

(63) Continuation of application No. 16/135,824, filed on Sep. 19, 2018, now Pat. No. 10,894,145.

(Continued)

(51) Int. Cl.
*A61M 25/01* (2006.01)
*A61M 25/00* (2006.01)
(Continued)

(52) U.S. Cl.
CPC ...... *A61M 25/0097* (2013.01); *A61M 25/005* (2013.01); *A61M 25/0054* (2013.01); *A61M 25/0136* (2013.01); *A61M 25/0147* (2013.01); *A61B 1/0052* (2013.01); *A61B 1/0057* (2013.01); *A61B 2017/003* (2013.01);
(Continued)

(58) Field of Classification Search
CPC .......... A61M 25/0133; A61M 25/0136; A61M 25/0147; A61B 1/0052
See application file for complete search history.

(56) References Cited

U.S. PATENT DOCUMENTS 5,489,270 A 2/1996 Van Erp
6,554,794 B1 * 4/2003 Mueller ............ A61M 25/0141
604/95.04

(Continued)

FOREIGN PATENT DOCUMENTS

WO WO 2016/138443 A2 9/2016

*Primary Examiner* — Laura A Bouchelle
(74) *Attorney, Agent, or Firm* — Crowell & Moring LLP (57) ABSTRACT

A steerable catheter having a hub with a control feature includes a semi-rigid catheter with the hub attached at the proximal end. The distal end of the catheter includes a distal tip and a flexible portion adjacent the distal tip. The catheter includes a working channel, and further includes a channel through which a tension member or wire extends to the distal tip. Tension in the wire causes the distal tip to deflect and be steered. The hub includes a fixed member attached to the catheter, an inner member that moves axially relative to the fixed member, and an outer member that rotates relative to the inner member and the fixed member. Rotation of the outer member results in translation of the inner member, which is attached to the tension member and provides for controlled steering of the distal tip.

19 Claims, 6 Drawing Sheets

Related U.S. Application Data (60) Provisional application No. 62/561,983, filed on Sep. 22, 2017.

(51) Int. Cl.
*A61B 17/00* (2006.01)
*A61B 1/005* (2006.01)

(52) U.S. Cl.
CPC .............. *A61B 2017/00323* (2013.01); *A61M 25/0043* (2013.01); *A61M 25/0138* (2013.01); *A61M 2025/015* (2013.01); *A61M 2025/0163* (2013.01)

(56) References Cited

U.S. PATENT DOCUMENTS

| | | | |
|---|---|---|---|
| 7,615,044 B2 * | 11/2009 | Scheibe | A61M 25/0136 604/95.04 |
| 7,803,130 B2 | 9/2010 | Ryan et al. | |
| 8,308,659 B2 | 11/2012 | Scheibe et al. | |
| 8,517,907 B2 * | 8/2013 | Chi Sing | A61N 5/1015 600/7 |
| 8,758,231 B2 | 6/2014 | Bunch et al. | |
| 9,095,682 B2 * | 8/2015 | Romoscanu | A61M 25/0133 |
| 9,149,607 B2 | 10/2015 | Scheibe et al. | |
| 9,308,349 B2 | 4/2016 | Rezac et al. | |
| 9,821,143 B2 * | 11/2017 | Kimmel | A61M 25/0127 |
| 10,894,145 B2 * | 1/2021 | Melsheimer | A61M 25/005 |
| 2009/0018500 A1 | 1/2009 | Carter et al. | |
| 2009/0177370 A1 | 7/2009 | Kawakita et al. | |
| 2010/0168665 A1 | 7/2010 | Skerven | |
| 2012/0053415 A1 | 3/2012 | Bunch et al. | |
| 2014/0276396 A1 | 9/2014 | Tegg | |
| 2014/0336573 A1 | 11/2014 | Yu et al. | |
| 2015/0073341 A1 | 3/2015 | Salahieh et al. | |
| 2015/0105655 A1 | 4/2015 | Tegg et al. | |
| 2015/0119800 A1 | 4/2015 | Neoh et al. | |
| 2015/0246206 A1 | 9/2015 | Schultz | |
| 2016/0004571 A1 | 2/2016 | Homsy et al. | |
| 2016/0058975 A1 | 3/2016 | Kimmel et al. | |
| 2016/0082226 A1 | 3/2016 | Eversull et al. | |
| 2017/0112361 A1 | 4/2017 | Surti et al. | |
| 2017/0251908 A1 | 9/2017 | Surti et al. | |
| 2018/0193174 A1 | 7/2018 | Pendleton et al. | |

* cited by examiner

STEERABLE CATHETER SYSTEM WITH HUB

CROSS-REFERENCE TO RELATED APPLICATIONS

This application is a continuation of U.S. application Ser. No. 16/135,824, filed Sep. 19, 2018, which claims priority from and the benefit of U.S. Provisional Application No. 62/561,983, filed Sep. 22, 2017, each of which is incorporated by reference herein in its entirety.

1. TECHNICAL FIELD

The present disclosure relates to medical devices. More particularly, the disclosure relates to a steerable catheter having a hub for steering the catheter.

2. BACKGROUND INFORMATION

Internal body cavities and body lumens often undergo blockages or include other circumstances where removal of blockages or treatment may be necessary. Endoscopic or other minimally invasive techniques may be used to treat these situations.

One type of treatment includes the use of catheters or other endoscopic devices that are inserted into the body lumen or cavity and toward the area where treatment is desired. Insertion of the endoscope to the target area can allow for visualization of the target area and a determination of the desired procedure and the specific location of the area to be treated.

Once a blockage has been identified, it is desirable to be able to remove the blockage without changing catheters. Passive catheters, however, make it difficult to visualize the target or pathway, navigate to a preferred site, and acquire a target.

One particular type of blockage where treatment is desirable is the case of kidney stones present in the kidneys. Removal of kidney stones typically requires a large working channel in the catheter where the kidney stones can pass through the working channel and out of the bladder.

Improvements can be made in the delivery of a catheter that can reach a target area and effectively visualize and remove blockages in the target area.

SUMMARY

The present disclosure provides a steerable catheter system that includes an elongate catheter having a proximal and distal end and a working channel extending from the proximal end to the distal end. The catheter includes a flexible portion of the catheter disposed adjacent the distal end of the catheter, the flexible portion being more flexible than a main body portion of the catheter. The catheter further includes a distal tip portion of the catheter disposed distally relative to the flexible portion.

The system may further include a tension member extending through a first accessory channel of the catheter, the tension member having a distal end that is fixedly attached to the distal end portion. Movement of the tension member proximally pulls the distal tip proximally and bends the flexible portion of the catheter.

The system further may further include a proximal hub assembly attached to the proximal end of the catheter. The proximal hub assembly includes a fixed hub member fixedly attached to the proximal end of the catheter. An axially moveable inner member is coupled to and surrounds a portion of the fixed hub, where the axially moveable member is restricted from rotational movement relative to the fixed hub and permitted to move in a proximal and distal direction relative to the fixed hub member.

A rotationally moveable outer member is coupled to and surrounds the axially moveable member and at least a portion of the fixed hub. The rotationally moveable member is restricted from longitudinal movement in the proximal and distal direction and permitted to rotate relative to the fixed hub and the axially moveable member.

Rotational movement of the outer member in a first rotational direction relative to the fixed hub results in axial translation of the inner member relative to the fixed hub in a first longitudinal direction. Rotational movement of the outer member in a second rotational direction that is opposite the first rotational direction results in axial translation of the inner member in a second longitudinal direction that is opposite the first longitudinal direction.

A proximal end of the tension member is attached to the inner member, and axial movement of the inner member in a proximal direction increases a tension in the tension member and bends the distal end of the catheter, and an axial movement of the inner member in a distal direction reduces the tension in the tension member.

In one embodiment, the fixed hub member includes a distal portion and a proximal portion, where the distal portion is in the form of a distally extending post. The inner member may be in the form of a sleeve and the outer member may be in the form of a sleeve.

The post of the fixed hub member may include at least one longitudinally extending rail that projects radially outward from the post, and the inner member may include a longitudinally extending slot that receives the rail and slides along the rail during axial movement of the inner member relative to the fixed hub.

The distal portion of the fixed hub may include a radially projecting annular collar, and the outer member may include an annular cavity that receives the collar and defines a bearing surface that bears against the collar during rotation of the outer member relative to the fixed hub.

The outer member may include an inner threaded portion, and the inner member may include an outer threaded portion, and the inner and outer threaded portions are correspondingly sized to cooperate with each other such that rotation of the outer member will cause the inner member to move axially. The inner threads and outer threads may be acme threads.

The inner member may include a separate first part and a second part that are joined together to define the inner member. The first part and the second part may be identically shaped. The outer member may include a separate first part and a second part that are joined together to define the outer member, and the first and second parts may be identically shaped. In one approach, the inner member may have a constant inner diameter.

The post of the fixed hub may have a tapered shape, where a distal end of the post has a smaller diameter than a proximal end of the post. Proximal movement of the inner member may result in a compressive force of the inner member on the post. The tapered shape may be a result of a changing wall thickness of the post, where an inner diameter of the post remains generally constant. The tapered shape may also be a result of a generally constant wall thickness of the post, where the inner diameter of the post decreases in a distal direction. The tapered shape may also be a combination of a distally decreasing inner diameter and a distally decreasing wall thickness. The tapered shape of the post may also help facilitate removal from a mold that forms the shape.

In one form, the first part of the inner member includes at least one peg and at least one recess, and the second part of the inner member includes at least one peg and at least one recess, and the peg of the first part is received in the recess of the second part, and the peg of the second part is received in the recess of the first part when the first and second parts are joined together. The first part of the outer member may include at least one peg and at least one recess, and the second part of the outer member may include at least one peg and at least one recess, and the peg of the first part is received in the recess of the second part, and the peg of the second part is received in the recess of the first part when the first and second parts are joined together.

In yet another embodiment a hub for attaching to a steerable catheter includes a fixed member having a distally extending post and a channel extending longitudinally therethrough. An axially moveable inner member may be coupled to and surround a portion of the post, where the axially moveable member may be restricted from rotational movement relative to the fixed member and permitted to move in a proximal and distal direction relative to the fixed member.

A rotationally moveable outer member may be coupled to and surround the axially moveable member and at least a portion of the fixed hub, where the rotationally moveable member may be restricted from longitudinal movement in the proximal and distal direction and permitted to rotate relative to the fixed hub and the axially moveable member.

The inner member may include external threads and the outer member may include internal threads, and the external and internal threads correspond to each other such that the external threads are received in the internal threads. Rotational movement of the outer member in a first rotational direction relative to the fixed hub results in axial translation of the inner member relative to the fixed hub in a proximal direction, and rotational movement of the outer member in a second rotational direction that is opposite the first rotational direction results in axial translation of the inner member in a distal direction.

A tension member may be coupled to the inner member and proximal movement of the inner member will increase a tension in the tension member and distal movement of the inner member will reduce the tension in the tension member.

In another embodiment a method for operating a steerable catheter includes delivering a steerable catheter having a proximal hub and a distal end, where the steerable catheter includes a flexible distal end and a tension member attached to the distal end and extending through the catheter. The method may include rotating a rotational outer member of the hub in a first rotational direction, where the outer member may be longitudinally fixed relative to the hub.

In response to rotating the outer member in the first rotational direction, the method may include axially translating an inner member in a proximal direction relative to the hub, where the inner member is rotationally fixed relative to the hub and surrounds a portion of the hub, and the inner member is housed within the outer member.

The tension member may be coupled to the inner member and in response to proximal translation of the inner member, the method may include increasing a tension on the tension member and flexing the distal end of the catheter.

In one form, rotation of the outer member is performed manually by gripping and twisting the outer member, and in response to releasing the outer member, the outer member maintains its rotational position.

In response to rotating the outer member in a rotational direction that is opposite the first rotational direction, the method may include translating the inner member distally and reducing the tension in the tension member.

In one approach, the outer member includes internal threading and the inner member includes external threading that cooperates with the internal threading, the outer member includes an annular groove and the hub includes an annular flange received within the groove, and the inner member includes a longitudinal groove and the hub includes a longitudinal rail received within the longitudinal groove.

DETAILED DESCRIPTION

The present invention provides a steerable catheter with a hub for easily controlling the distal end of the catheter to visualize and acquire a target. The disclosure provides also for methods of treatment. The materials, methods, and examples disclosed herein are illustrative only and not intended to be limiting. The disclosed figures are not necessarily to scale.

All publications, patent applications, patents, and other references mentioned herein are incorporated by reference in their entirety. Unless otherwise defined, all technical and scientific terms used herein have the same meaning as commonly understood by one of ordinary skill in the art to which this disclosure pertains. In the case of conflict, the present document and definitions will control.

The terms "proximal" and "distal" and derivatives thereof will be understood in the frame of reference of a medical physician using the device. Thus, proximal refers to locations closer to the physician and distal refers to locations farther away from the physician (e.g., deeper in the patient's vasculature).

Figure 1:
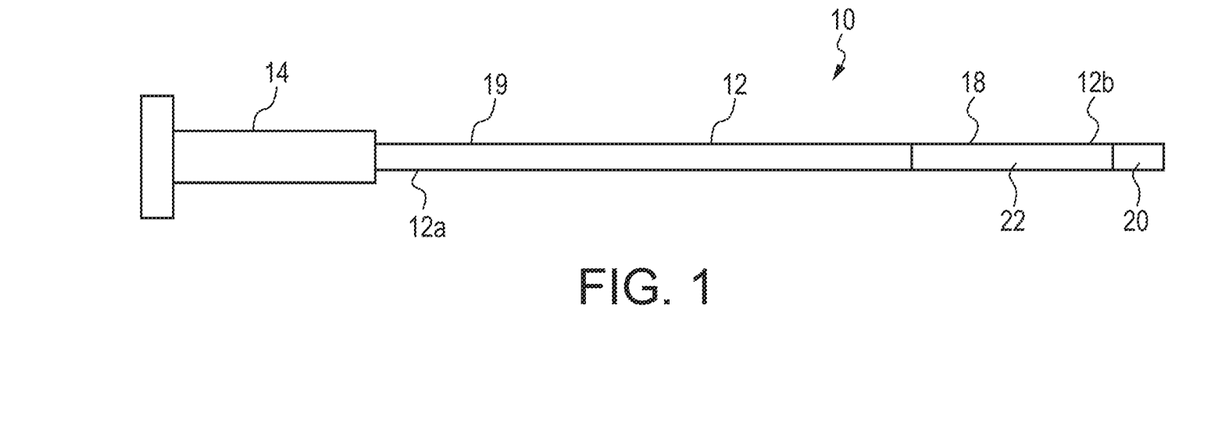
FIG. 1 illustrates a schematic view of a steerable catheter system including a steerable catheter and a hub assembly.

FIG. 1 illustrates a system 10 for navigating to an internal body vessel and providing treatment to the body vessel. The system includes a steerable catheter 12 and a hub 14 attached to the steerable catheter 12 than provides control for the steerable catheter 12. The catheter 12 has a generally elongate shape and includes a proximal end 12a and a distal end 12b.

Figure 2:
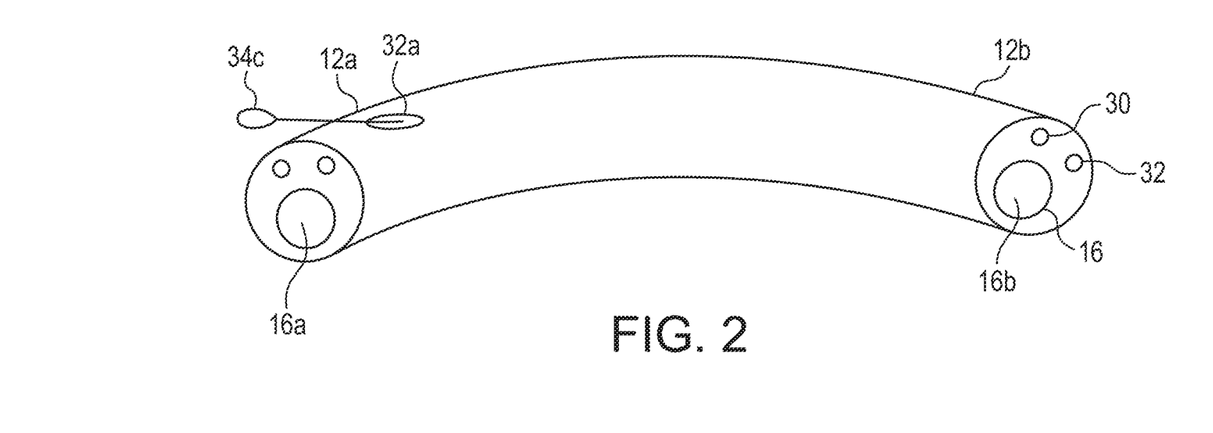
FIG. 2 illustrates a channels extending through the catheter from the proximal end to the distal end and a tension member extending out of the side of the catheter at the proximal end.

As illustrated in FIG. 2, the catheter 12 further includes a working channel 16 that extends fully through the catheter 12 from the proximal end 12a to the distal end 12b, and defines a proximal opening 16a and a distal opening 16b.

The catheter 12 is preferably made from a semi-rigid material that has sufficient pushability to allow for the catheter 12 to be delivered through a narrow body lumen or other strictures and toward a target site. The overall size and length of the catheter 12 may be selected depending on the type of procedure to be performed and the needs of the patient.

With reference to FIG. 1, the catheter 12 further includes a distal portion 18, which includes the distal end 12b, and a proximal portion 19 that includes the proximal end 12a. The distal portion 18 further includes a distal tip 20 that defines the distal end 12b. The distal tip 20 is preferably in the form of a semi-rigid material, similar to the proximal portion 19.

The distal portion 18 further includes a flexible portion 22 that is disposed proximally relative to the distal tip 20. The flexible portion 22 is preferably made from a more flexible material than the distal tip 20 and the proximal portion 18.

The proximal portion 19 extends from the proximal end 12a up to the flexible portion 22. Thus, the overall catheter includes the proximal portion 19, which meets the flexible portion 22, which meets the distal tip 20. The flexible portion 22 is configured to allow the distal tip 20 to be bent or oriented at an angle relative to the proximal portion 19, via bending of the flexible portion 22. It will be appreciated that the catheter 12 may be curved or slightly bent overall during use, so references to the bending of the distal tip 20 relative to the proximal portion 19 are made assuming a straight configuration of the proximal portion 19, and other bending of the proximal portion 19 may increase the relative angle between the distal tip 20 and the proximal portion 19.

With reference to FIG. 2, the catheter 12 further includes additional channels extending from the proximal end 12a toward the distal end 12b. In one embodiment, the catheter includes an accessory channel 30 that extends the length of the catheter 12 from the proximal end 12a to the distal end 12b. The accessory channel 30 is smaller than the working channel 16, and can be used to house a visualization device, such as a camera or the like. Accordingly, the accessory channel 30 preferably includes an open distal end so that the camera can view the target site.

Figure 3:
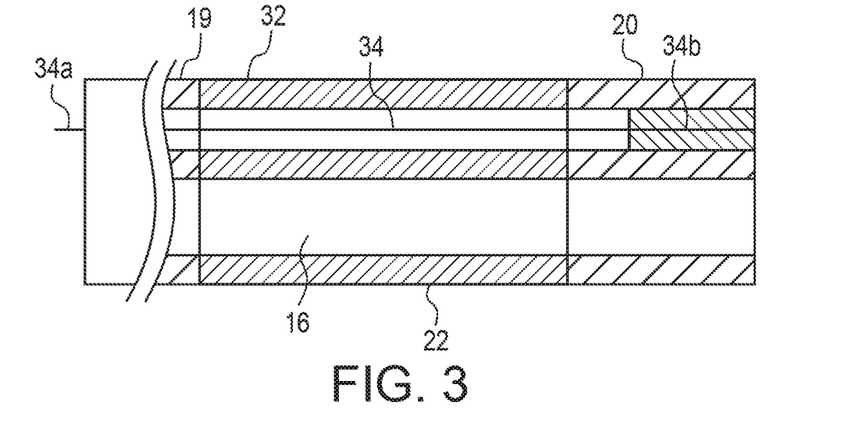
FIG. 3 is a cross-sectional schematic view of a distal portion of the catheter illustrating the tension member extending through a tension channel and being attached to a distal tip of the catheter.

With reference to FIG. 3, in addition to the working channel 16 and the accessory channel 30, the catheter may also include a tension channel 32 sized and configured to allow a tension member 34 to pass through the tension channel 32.

Figure 4:
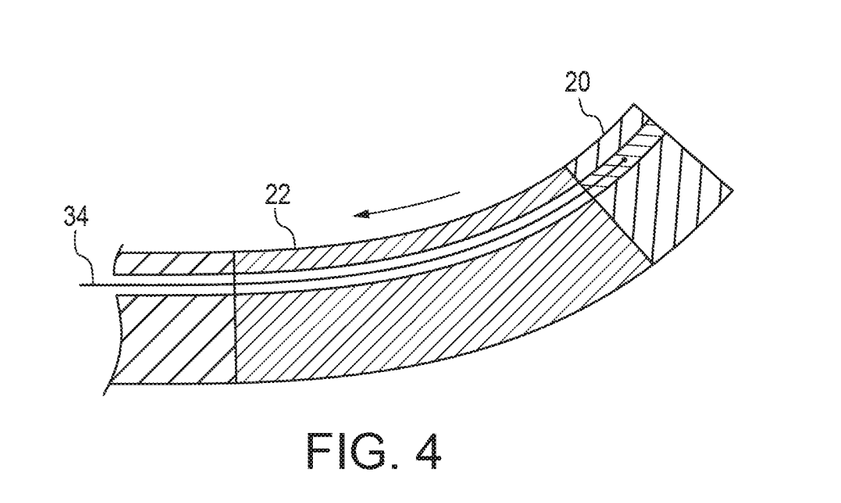
FIG. 4 is a schematic view of the tension member being put in the tension and a flexible portion of the catheter flexing, and the distal tip being in a bent state.

The tension channel 32 may extend fully through the catheter 12 in one form, or it may terminate prior to the distal end 12b of the catheter 12. The tension member 34 is configured to be able to be pulled through the tension channel 32 to cause the distal tip 20 to be pulled toward the proximal end 12a, thereby causing the distal tip 20 to bend relative to the proximal portion 19. The distal tip 20 being in a bent state is illustrated in FIG. 4.

In order to pull the distal tip 20 by pulling on the tension member 34, the tension member 34 is fixedly attached to the distal tip 20. In one approach, the tension member 34 is in the form of a thin and flexible wire that is sized to correspond to the diameter of the tension channel 32. The wire can be a solid core wire, braided wire, coiled wire, flat wire, or other known flexible wire. The wire may have a cross-sectional shape that is generally circular, round, oval, ellipsoid, square, rectangular, polygonal, or other known cross-sectional shapes. The tension member 34 can be made relatively thin, as it is not necessary for the tension member 34 to have pushability, because the pushability of the system 10 is provided by the catheter 12.

The tension member 34 has a proximal end 34a and a distal end 34b. The distal end 34b is attached to the distal tip 20 of the catheter 12, as shown in FIG. 3. The distal end 34b may be attached via known methods for fixing a wire within a catheter channel, including adhesives, bonding, welding, crimping a slug onto the wire, clamping the wire, or the like. In one approach, the tension channel 34 defines an open distal end at the distal end 12b of the catheter 12, and the distal end 34b of the tension member 32 is located adjacent the distal end 12b of the catheter 12, and the distal opening of the tension channel 32 is filled with an adhesive that will bond and fix the distal end 34b of the tension member within the tension channel 32.

Figure 5:
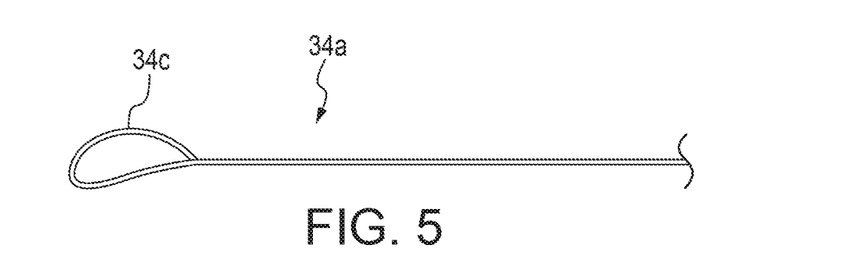
FIG. 5 illustrates a proximal end of the tension member having a loop.

The proximal end 34a of the tension member 34 is configured for being attached to the hub 14. In one approach, as shown in FIGS. 2 and 5, the proximal end 34a may be in the form of an attachment mechanism 34c, such as a loop or a hook, that is arranged to cooperate with corresponding structure of the hub 14, which will be further described below.

The catheter 12 may further include a passageway 32a that provides access to the tension channel 32 through the side of the catheter 12, such that the proximal end 34a of the tension member 34 can extend out of the side of the catheter 12 near the proximal end 12a, as shown in FIG. 2. The proximal end 34a of the tension member 34 may be attached to the hub 14, which is attached to the proximal end 12a of the catheter 12.

The catheter 12 has been described as being semi-rigid. In one approach, the catheter 12 is constructed as a coiled wire that defines the working channel 16, and an outer sleeve is placed over the coiled wire, with the sleeve defining the accessory channel 30 and the tension channel 32. The coiled wire may provide the semi-rigidness of the catheter 12. However, other multi-channel constructions may also be used. In another approach, the catheter 12 may be extruded and homogenous in the proximal portion 19. Different materials may be used to affect the stiffness and flexibility of the proximal portion 19 and the flexible portion 22, as well as the distal tip 20. In one approach, the proximal portion 19 and the distal tip 20 have the same stiffness, and the flexible portion 22 is more flexible. The stiffness/flexibility of the different portions of the catheter 12 may also be affected by the construction of the coiled wire, with a greater coil spacing being used in the flexible portion 22.

Turning now to FIGS. 6-9, with regard to the hub 14, the hub 14 operates as a control feature that can provide and easily maintain tension on the tension member 32 to adjust the orientation of the distal tip 20 to aid in visualizing and acquiring a target at the target area of the body lumen.

Figure 7:
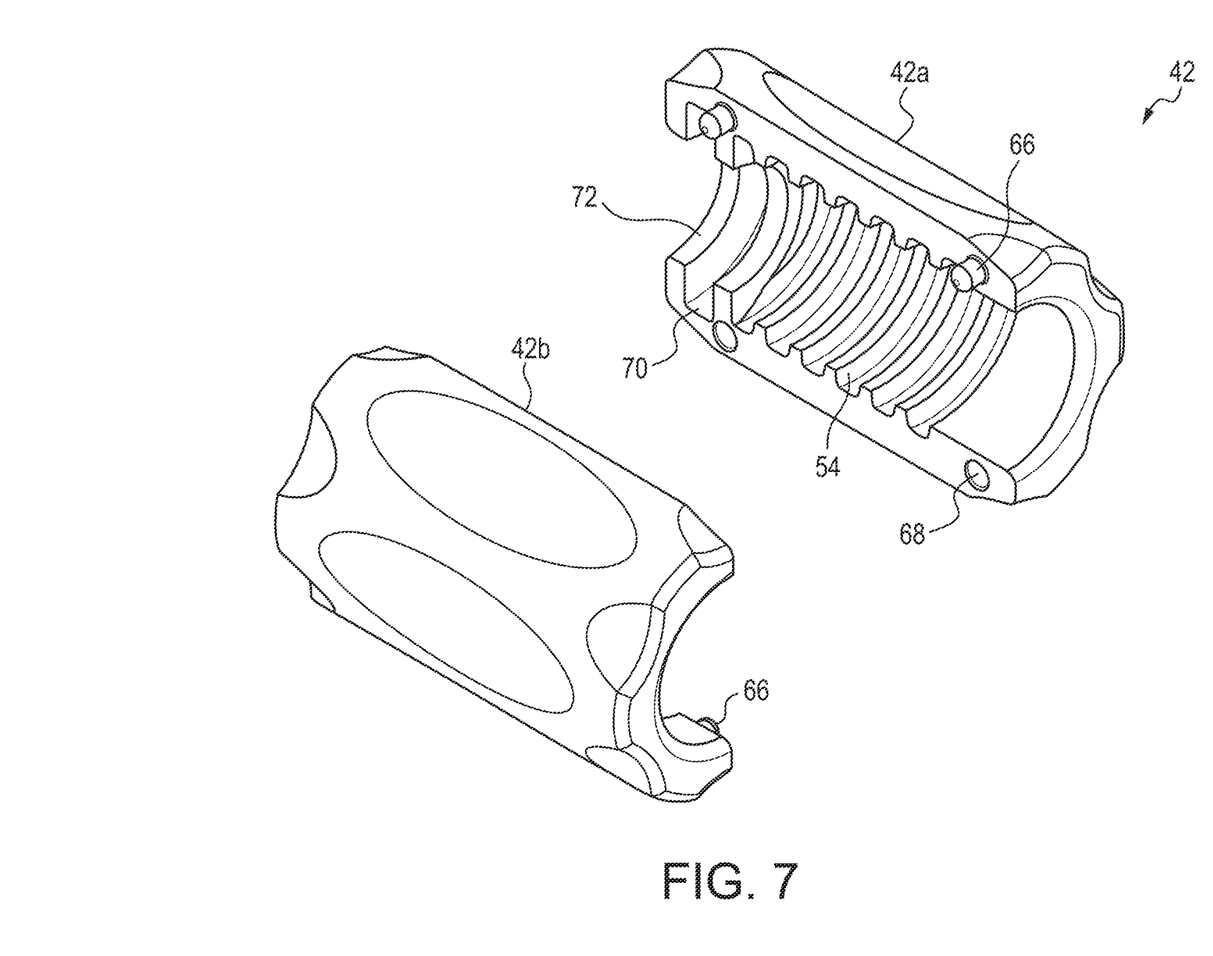
FIG. 7 illustrates an outer member of the hub assembly in two pieces and having internal threading and an annular cavity.
Figure 8:
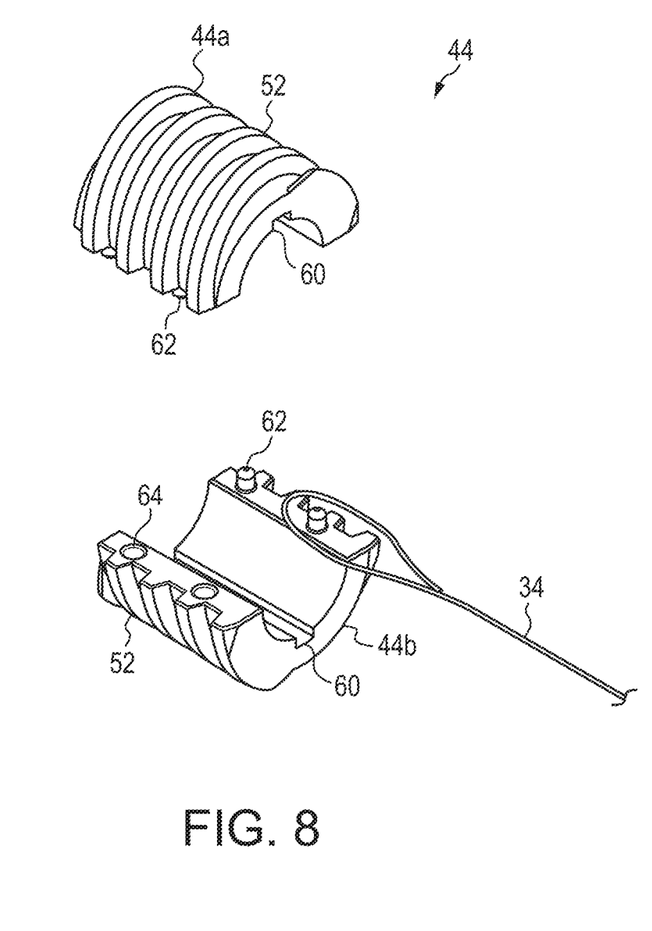
FIG. 8 illustrates an inner member of the hub assembly in two pieces and having external threading an axially extending slots.

The hub 14 may include three main components, including a fixed member 40 (FIG. 6), a rotating dial or outer member 42 (FIG. 7), and an axially moveable inner member 44 (FIG. 8). The tension member 34 is attached to the inner member 44, such that axial movement of the inner member 44 away from the distal tip 20 will put the tension member 34 in tension, causing the distal tip 20 to buckle or flex and change its orientation. Movement of the inner member 44 will be further described below.

Figure 6:
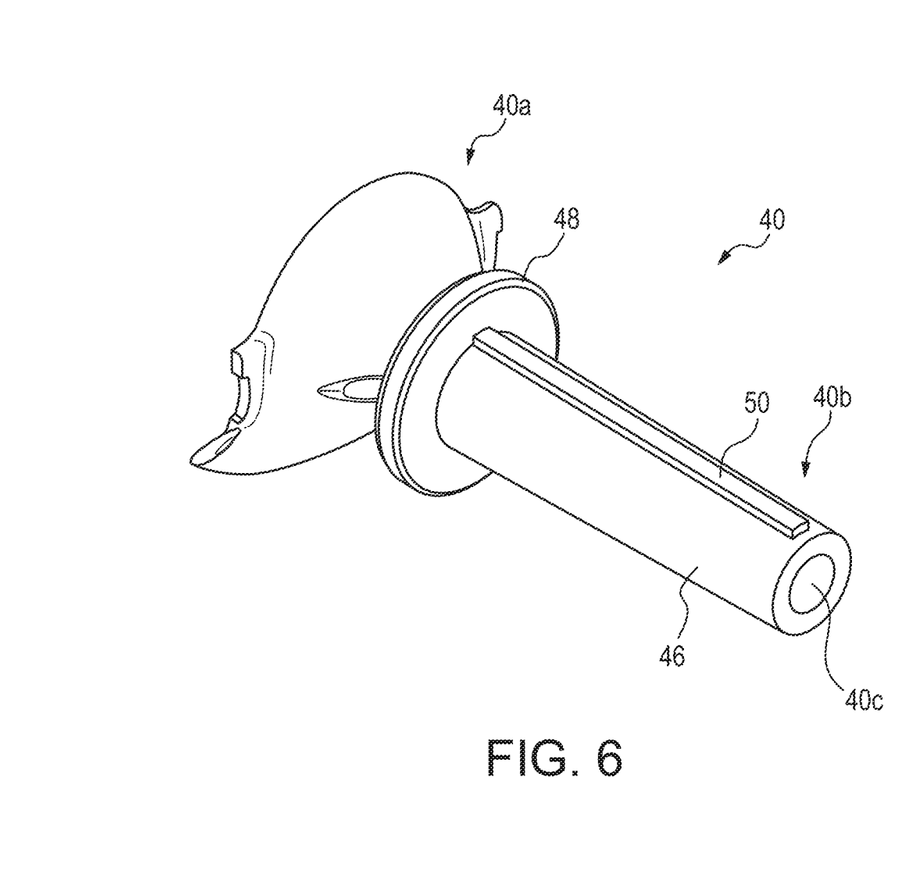
FIG. 6 illustrates a fixed member of the hub assembly having a proximal portion and post extending distally from the proximal portion.

With reference to FIG. 6, the fixed member 40 includes a proximal portion 40a and a distal portion 40b. The proximal portion 40a may in the form of a graspable cup having a proximally facing recess for aiding in manipulating and controlling the orientation of the fixed member 40. Controlling the orientation of the fixed member 40 will control the orientation of the catheter 12 when the catheter and fixed member 40 are attached to each other. The catheter 12 may be fixed to the distal portion 40b, with the proximal end 12b being received by the distal portion 40b.

The distal portion 40b may include a distally extending post 46 that extends longitudinally away from the proximal portion 40a. The fixed member 40 may include a channel 40c that extends fully through the fixed member 40 and is sized to receive the proximal end 12a of the catheter 12 when then hub 14 and catheter 12 are attached to each other. Thus, the channel 40c provides access to the working channel 16 of the catheter 12, as well as access to the accessory channel 30, when the proximal end 12a of the catheter 12 is attached to the distal portion 40b.

Figure 9:
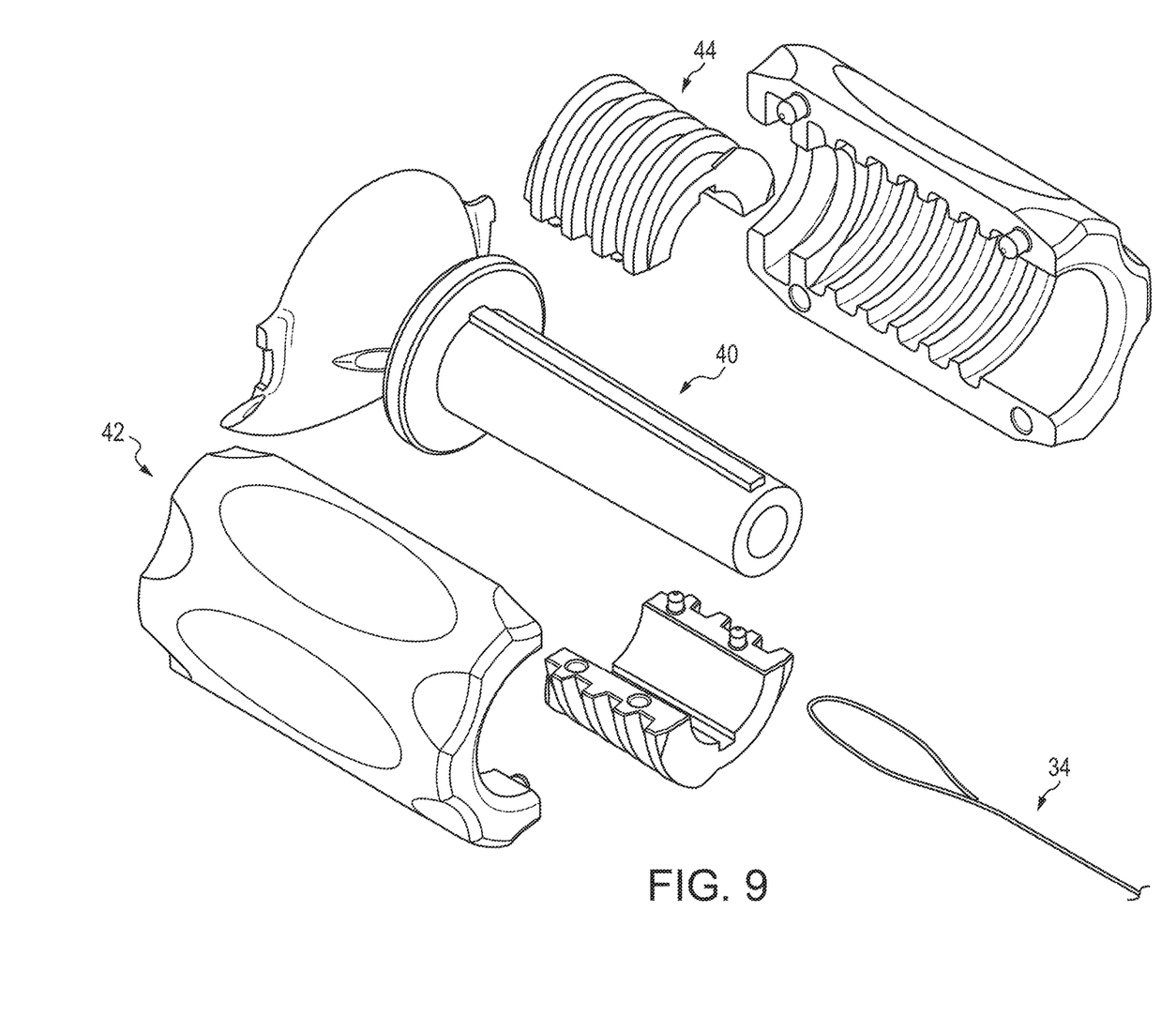
FIG. 9 is an exploded view of the hub assembly including the fixed member, two halves of the inner member, two halves of the outer member, and the tension member, where the inner member is assembled to surround the post of the fixed member, and the outer member is assembled to surround the inner member, where the threads of the inner member will engage the threads of the outer member.

FIG. 9 illustrates an exploded view of the fixed member 40, the inner member 44, and the outer member 42. When assembled, the inner member 44 surrounds the post 46 and is restricted from rotational movement relative to the post 46. The outer member 42 surrounds the inner member 44 and the post 46, and is restricted form axial movement relative to the post 46. The inner member 44 and outer member 42 are coupled to each other via spiral threading, such that rotation of the outer member 42 will cause translation of the inner member 44 due to the respective axial and rotational restrictions on the outer member 42 and inner member 44.

With reference again to FIG. 6, the distal portion 40b further includes features for restricting axial movement of the outer member 42 and rotational movement of the inner member 44. In one approach, the distal portion 40b includes a radially projecting annular flange 48. The flange 48 may have a disc shape. The flange 48 is configured to be received in corresponding structure of the outer member 44, such that that outer member 44 may rotate relative to the fixed member 40 and the flange 48, but the outer member 44 will be prevented from moving axially relative to the fixed member 40. The flange 48 is disposed at the base of the post 46, and adjacent the proximal portion 40a. The post 46 extends distally from the flange 48.

In one approach, the post 46 may include one or more, and preferably a pair of, longitudinally extending rails 50 that extend radially outward from an outer surface of the post 46. The rails 50 are configured to cooperate with corresponding structure of the inner member 44 to restrict rotational movement of the inner member 44 relative to the post 46 and the fixed member 40, while permitting axial movement along the rails 50.

The rails 50 may have a generally square or rectangular profile, or they may have a rounded profile or triangular profile or other profile that can sufficiently restrict rotational movement of the inner member 44 around the post 46.

With reference to FIGS. 7 and 8, the outer and inner members 42 and 44 may be in the form of nested sleeves, with the inner member 44 fitting within the outer member 42. The outer and inner members 42 and 44 may have a shape generally resembling a cylinder. In one approach the inner member 44 is longitudinally shorter than the outer member 42, such that there is open space proximal and distal to the inner member 44 within the outer member 42 when the inner member 44 is axially centered within the outer member 42.

The inner member 44 and outer member 42 have corresponding structure such that they will cooperate with each to convert rotational movement to axial movement. More particularly, the inner member 44 includes external spiral threading 52, and the outer member 42 includes corresponding internal spiral threading 54.

In one approach, the threads are in the form of Acme threads having a trapezoidal profile and providing a high level of axial strength. However, other thread profiles could also be used.

The number of threads of the external threading 52 of the inner member 44 may be less than the number of threads of the internal threading 54 of the outer member 42, because the inner member 44 is configured to move axially within the threads of the outer member 42. However, in another approach, the number of threads could be the same or the inner member 44 may have more threads than the outer member 42, and the inner member 44 may extend distally beyond the outer member 42 in an un-tensioned state and translate proximally into the outer member 42 to provide tension.

Both the outer member 42 and the inner member 44 may be formed as the combination of two separate pieces. Thus, the outer member 42 may be formed by the combination of a first outer member half 42a and a second outer member half 42b. The inner member 44 may be formed by the combination of a first inner member half 44a and a second inner member half 44b. In a preferred form, the halves 44a and 44b are the same shape and have the same features, such that they are interchangeable and effectively identical. The halves 42a and 42b may be similarly arranged relative to each other, such that they are essentially identical.

For example, with reference to the inner member halves 44a and 44b, each includes that same external thread profile. Each half 44a and 44b includes a longitudinal slot 60 sized and arranged to correspond to the size and shape of the longitudinal rail 50 such that the rail 50 may be received in the slot 60.

Each half 44a and 44b may include, on a first lateral side, at least one peg 62, and preferably two pegs 62. On the opposite second lateral side, the halves 44a and 44b may include a peg recess 64 sized to correspond to the peg or pegs 62 on the first lateral side. Thus, when the halves 44a and 44b are assembled, the pegs 62 of the first half 44a will be received in the peg recesses 64 of the second half 44b. The halves are arranged such that they can be assembled in only one way, thereby resulting in a complete and continuous external thread profile.

The halves 42a and 42b are arranged in a similar fashion, where each half is substantially identical and includes pegs 66 on a first lateral side and recesses 68 on the opposite lateral side. Further, each half includes a semi-annular slot 70 that, when combined, define an annular cavity 72 that is sized and configured to receive the annular flange 48 of the fixed member 40.

It will be appreciated that the halves of the inner member 44 and the outer member 42 may be different in some approaches. For example, one half may include only one peg, while the other has two, or each half may include one peg, but at different locations, where they will each still be received in a recess. In another approach, the halves of the inner member 44 and/or outer member 42 may be free from pegs and recesses, and they may be joined via other known methods, so long as the combination of the halves results in a continuous thread profile around or within the inner member 44 and outer member 44.

In another approach, the inner member 44 may be made from a single, unitary, monolithic, or homogenous structure rather than as two assembled halves. In this approach, the inner member 44 may still be assembled with the fixed member 40 by sliding over the post 46 along the rails 50.

In another approach, the inner member 44 and/or outer member 42 may be formed by more than two pieces. However, for the purposes of further discussion, the inner member 44 and outer member 42 will be described as being in the form of two assembled halves.

To assemble the system 10, the fixed member is attached to the proximal end 12a of the catheter 12. The two halves 44a and 44b of the inner member 44 are combined around the fixed member 40 and the post 46, with the rails 50 being received in the slots 60 of the inner member 44. The proximal end 34a of the tension member 34 may be sandwiched or compressed between the two halves 44a, 44b to attach the tension member 34 to the inner member 44. In one approach, a loop at the proximal end 34a of the tension member 34 is placed around one or more of the pegs 62 on one side of the inner member 44 (FIG. 8). In another approach, the proximal end 34a of the tension member 34 may be attached to the inner member using other known methods, such as embedding, adhesive, bonding, welding, or the like. In another approach, a hook or other mechanical connection could be used to attach to the proximal end 34a of the tension member 34. The halves 44a and 44b may be optionally fixed to each other via bonding or some other method, or they may be left in a state that they can be easily de-coupled.

After assembling the inner member 44, the outer member 42 is assembled in a similar fashion over the inner member 44 and the fixed member 40. The external threads 52 of the inner member 44 are received in the internal threads 54 of the outer member 42, and the flange 48 is received within the semi-annular slots 70 that form the annular cavity 72 of the outer member 42. During assembly, if the tension member 34 has been attached to the inner member 44 prior to the outer member 42 being assembled, it is preferable for the inner member to be disposed distally away from the flange 48, such that there is space between the inner member 44 and the flange 48. Thus, the inner member 44 may move axially toward the flange 48 to tension the tension member 34.

Once the outer member 42 is assembled, the outer member halves 42a, b may be fixed together via adhesive or bonding, or via a removable clip or other such mechanism that will hold the outer member 42 together. The inner member 44 can be retained in its assembled condition via the outer member 42 without additional retention methods.

Once assembled, the tension member 34 may be tensioned by rotating the outer member 42 relative to the fixed member 40. The flange 48 and annular cavity 72 will define bearing surfaces that allow the outer member 42 to rotate, but restricting the outer member 42 from moving axially. The inner member 44, due to its restriction on rotational movement caused by the rails 50 and the slots 60, will respond to the rotation of the outer member 42 by moving axially. The direction of rotation of the outer member 42 will determine the direction of axial movement of the inner member 44. In one approach, when looking distally, clockwise rotation of the outer member 42 will cause proximal translation of the inner member 44, thereby putting the tension member 34 in tension, and counter-clockwise rotation causes distal movement and a reduction in tension. It will be appreciated that the thread direction can be varied to result in counter-clockwise rotation resulting in tension.

The degree of rotation permitted depends on the arrangement of the threads and the available length of the travel of the inner member 44 within the outer member 42. In one approach, the outer member 42 may be allowed to rotate about 180 degrees between terminal positions of the inner member 44 within the outer member 42. It will be appreciated that other amounts of permitted rotation could also be achieved by varying the sizes of the inner member 44 relative to the outer member 42, or by altering the threads.

After rotating the outer member 42 and putting the tension member 34 in tension, the outer member 42 can be released, and it can be held in place and/or restricted from reversing in response to the tension in the tension member 34 due to the engagement of the threads. In one approach, the post 46 may have a tapered or frusto-conical profile, such that it is wider near the flange 48 than at its distal end. In this approach, the inner diameter of the post 46 may be greater at the proximal end than at the distal end. Alternatively, the inner diameter of the post 46 may be generally constant, and the wall of the post may have a greater thickness near the proximal end relative to the distal end. In another approach, the wall of the post 46 may decrease distally and the inner diameter of the post 46 may also decrease distally. Thus, when the inner member 44 moves axially toward the flange 48, the post 46 and the inner member 44 will become wedged together, further retaining the position of the inner member 44 and the outer member 42 after rotating to a particular orientation. The tapered shape of the post 46 may help facilitate removal from a mold used to create the shape of post 46. However, it will be appreciated that the post 46 may be generally cylindrical and without a taper, and the inner member 44 may still be retained in its axial position after rotating and releasing the outer member 42 due to the engagement of the threads and the axial force on the threads caused by the tension in the tension member 34. Similarly, the inner member 44 may be retained on a tapered post 46 without applying a compressing force on the post 46 or being wedged with the post.

When the tension member 34 is put in tension, the distal tip 20 of the catheter 12 will be pulled in a proximal direction. The tension channel 32 that contains the tension member 34 is offset relative to the center of the catheter 12, so the tension is applied to one side of the catheter 12. The distal tip 20 will generally bend to the same side as the tension channel 32 in response to tension in the tension member 34. More particularly, the flexible portion 22 of the distal portion 18 will be compressed along the tension channel 32, such that its length is reduced on that side, which causes the flexible portion 22 to bend. The distal tip 20 and proximal portion 19, being more rigid than the flexible portion 22 will generally not undergo any substantial compression in response to tension, because the flexible portion 22 is less resistant to a shape change. However, it will be appreciated that some bending or compression of the material in the proximal portion 19 and the distal tip 20 may also occur.

The catheter 12 is resiliently biased toward a nominal state, such that release of the tension in the tension member 34 will result in catheter returning toward the original shape as it was prior to putting the tension member 34 in tension. This tensioning can be repeated as necessary to adjust the orientation of the distal tip 20 relative to the proximal portion 19. Thus, in the event that the distal tip 20 has bent farther than desired, rotating the outer member 42 in the opposite rotational direction and reducing the tension in the tension member 34 will thereby reduce the degree of the bend of the catheter 12.

Thus, the distal tip 20 can be adjusted on demand relative to the remainder of the catheter 12. Further, the catheter 12, including a bent distal tip 20, can also be rotated and adjusted by rotating the fixed member 40 of the hub 14, giving the operator control over visualization and treatment of a target area while the tip 20 remains bent.

Once a target has been identified, additional medical devices can be delivered through the working channel to treat the target area, such as a kidney stone breaker and/or basket in the case of kidney stones. The distal tip 20 can be further steered to direct these medical devices toward the desired area with increased precision.

Having described the structure of the system 10 and its various components, use of the system 10 will now be further described.

The catheter 12 is introduced into an orifice of the body and delivered to a general target area through the body lumen. The catheter 12 may be pushed by the operator via the hub 14. The catheter 12 may be monitored during insertion toward the target area using known monitoring methods.

Upon reaching the target area, the catheter 12 can be manipulated to steer the distal end 12b. More particularly, the outer member 42 may be rotated relative to the fixed member 40 in a first rotational direction. In response to rotating the outer member 42, the inner member 44 will translate axially toward the operator in a proximal direction.

Rotation of the outer member 44 will cause the internal threads 54 to rotate. The internal threads 54 are engaged with the external threads 52 of the inner member 44. Furthermore, the outer member 44 will not be allowed to move axially, because the flange 48 is disposed within the cavity 72 of the outer member. The flange 48, however, allows the outer member 42 to rotate.

The internal threads 54 will bear against the external threads 52 of the inner member 44, forcing the inner member 44 to move axially through the axially stationary outer member 42 due to the engagement between the corresponding threads.

The axial translation of the inner member 44 occurs along the rail 50, where the inner member 44 and its slot 60 will slide along the 50 and bear against the rail 50. The rail 50 will limit the inner member 44 from rotating. Thus, rotation of the outer member 42 will cause the inner member 44 to translate axially.

As the inner member 44 translates axially, the tension member 34, which is attached to the inner member 44, will be pulled along with the inner member 44. The distal end 34b of the tension member 34 is fixed to the distal tip 20 of the catheter, such that the proximal movement of the tension member 34 along with the inner member 42 puts the tension member 34 in tension, which pulls the distal tip 20 proximally. This proximal pulling force causes the distal tip 20 to bend via the flexible portion 22.

During rotation of the outer member 42 and the resulting bending of the distal tip 20, the orientation of the distal tip 20 may be monitored using known methods. When the desired orientation is achieved, the rotation of the outer member 42 may be stopped. The outer member 42 may be released but will remain at its rotational position, which in turn maintains the distal tip 20 at its orientation.

The outer member 42 may be rotated in a second rotational direction that is opposite the first rotational direction, with the opposite movement of the inner member 44 occurring in response. Thus, the inner member 44 will move distally, and tension in the tension member 34 will be reduced, allowing the distal tip 20 to return toward a straight orientation.

The outer member 42 can be continually rotated in different directions to cause the catheter 12 to bend more or bend less, depending on the desired orientation of the catheter 12 during use.

When the catheter 12 is in a desired bent shape, the entire catheter 12 can be rotated by rotating the fixed member 40 without manipulating the outer member 42 relative to the fixed member. Thus, the degree of the bend in the catheter 12 will remain the same, but the catheter 12 will point to a different location.

When the catheter 12 is in its desired orientation, further procedures may be carried out through the working channel 16. When the desired procedures are complete, the outer member 42 can be rotated in the second rotational direction fully such that the tension is released and the catheter 12 can return to its straight configuration, and the catheter 12 can be removed from the body.

While the present invention has been described in terms of certain preferred embodiments, it will be understood that the invention is not limited to these disclosed embodiments as those having skill in the art may make various modifications without departing from the scope of the following claims.

We claim:

1. A steerable catheter comprising:
an elongate catheter having a proximal and distal end and a working channel extending from the proximal end to the distal end;
a flexible portion of the catheter disposed adjacent the distal end of the catheter, the flexible portion being more flexible than a proximal main body portion of the catheter;
a distal tip portion of the catheter disposed distally relative to the flexible portion;
a tension member extending through a first accessory channel of the catheter, the tension member having a distal end that is fixedly attached to the distal tip portion, wherein movement of the tension member proximally pulls the distal tip proximally and bends the flexible portion of the catheter;
a proximal hub assembly attached to the proximal end of the catheter, the proximal hub assembly comprising:
a fixed member fixedly attached to the proximal end of the catheter, wherein the fixed member includes a distal portion and a proximal portion, wherein the distal portion of the fixed member is in the form of a distally extending post;
an axially moveable inner member coupled to and surrounding a portion of the fixed member, the axially moveable member restricted from rotational movement relative to the fixed member and permitted to move in a proximal and distal direction relative to the fixed member;
a rotationally moveable outer member coupled to and surrounding the axially moveable member, the rotationally moveable member restricted from longitudinal movement in the proximal and distal direction and permitted to rotate relative to the fixed member and the axially moveable member;
wherein rotational movement of the outer member in a first rotational direction relative to the fixed member results in axial translation of the inner member relative to the fixed member in a first longitudinal direction, and rotational movement of the outer member in a second rotational direction that is opposite the first rotational direction results in axial translation of the inner member in a second longitudinal direction that is opposite the first longitudinal direction;

wherein a proximal end of the tension member is attached to a distal end of the inner member, and axial movement of the inner member in a proximal direction increases a tension in the tension member and bends the distal end of the catheter, and an axial movement of the inner member in a distal direction reduces the tension in the tension member; and configured wherein the proximal movement of the inner member results in a compressive force of the inner member on the post.

2. The steerable catheter of claim 1, wherein the inner member is in the form of a sleeve and the outer member is in the form of a sleeve.

3. The steerable catheter of claim 2, wherein the post of the fixed member includes:

a radially projecting annular flange; and at least one longitudinally extending rail that projects radially outward from the post, and the inner member includes a longitudinally extending slot that receives the rail and slides along the rail during axial movement of the inner member relative to the fixed member.

4. The steerable catheter of claim 2, wherein the distal portion of the fixed member includes a radially projecting annular collar, and the outer member includes an annular cavity that receives the collar and defines a bearing surface that bears against the collar during rotation of the outer member relative to the fixed member.

5. The steerable catheter of claim 2, wherein the outer member includes an inner threaded portion, and the inner member includes an outer threaded portion, and the inner and outer threaded portions are correspondingly sized to cooperate with each other such that rotation of the outer member will cause the inner member to move axially.

6. The steerable catheter of claim 2, wherein the inner member includes a separate first part and a second part that are joined together to define the inner member.

7. The steerable catheter of claim 6, wherein the first part and the second part are identically shaped.

8. The steerable catheter of claim 2, wherein the outer member includes a separate first part and a second part that are joined together to define the outer member.

9. The steerable catheter of claim 5, wherein the inner threads and outer threads are acme threads.

10. The steerable catheter of claim 3, wherein the inner member has a constant inner diameter.

11. The steerable catheter of claim 10, wherein the post of the fixed member has a tapered shape, where a distal end of the post has a smaller diameter than a proximal end of the post.

12. The steerable catheter of claim 11, wherein proximal movement of the inner member results in a compressive force of the inner member on the post.

13. The steerable catheter of claim 6, wherein the first part of the inner member includes at least one peg and at least one recess, and the second part of the inner member includes at least one peg and at least one recess, and the peg of the first part is received in the recess of the second part, and the peg of the second part is received in the recess of the first part when the first and second parts are joined together.

14. The steerable catheter of claim 8, wherein the first part of the outer member includes at least one peg and at least one recess, and the second part of the outer member includes at least one peg and at least one recess, and the peg of the first part is received in the recess of the second part, and the peg of the second part is received in the recess of the first part when the first and second parts are joined together.

15. A hub for attaching to a steerable catheter, the hub comprising:

a fixed member having a distally extending post and a channel extending longitudinally therethrough within the distally extending post;

an axially moveable inner member coupled to and surrounding a portion of the post, the axially moveable member restricted from rotational movement relative to the fixed member and permitted to move in a proximal and distal direction relative to the fixed member;

a rotationally moveable outer member coupled to and surrounding the axially moveable member, the rotationally moveable member restricted from longitudinal movement in the proximal and distal direction and permitted to rotate relative to the fixed member and the axially moveable member;

wherein the inner member includes external threads and the outer member includes internal threads, and the external and internal threads correspond to each other such that the external threads are received in the internal threads;

wherein rotational movement of the outer member in a first rotational direction relative to the fixed member results in axial translation of the inner member relative to the fixed member in a proximal direction, and rotational movement of the outer member in a second rotational direction that is opposite the first rotational direction results in axial translation of the inner member in a distal direction;

wherein a tension member is coupled to the inner member and proximal movement of the inner member will increase a tension in the tension member and distal movement of the inner member will reduce the tension in the tension member;

wherein the proximal movement of the inner member results in a compressive force of the inner member on the post.

16. A method for operating the steerable catheter of claim 1, the method comprising:

rotating the outer member of the hub in a first rotational direction;

in response to rotating the outer member in the first rotational direction, axially translating the inner member in a proximal direction relative to the hub; and in response to proximal translation of the inner member, increasing a tension on the tension member and flexing the distal end of the catheter.

17. The method of claim 16, wherein rotation of the outer member is performed manually by gripping and twisting the outer member, and in response to releasing the outer member, the outer member maintains its rotational position.

18. The method of claim 16, wherein, in response to rotating the outer member in a rotational direction that is opposite the first rotational direction, translating the inner member distally and reducing the tension in the tension member.

19. The method of claim 16, wherein the outer member includes internal threading and the inner member includes external threading that cooperates with the internal threading, the outer member includes an annular groove and an annular flange on the fixed member is received within the groove.

* * * * *